United States Patent
Matsushima et al.

(10) Patent No.: US 9,211,215 B2
(45) Date of Patent: Dec. 15, 2015

(54) DISPOSABLE DIAPER WITH GATHER INCLUDING ELONGATED STRETCHABLE MEMBERS

(75) Inventors: Hideki Matsushima, Kagawa (JP);
Satoru Sakaguchi, Kagawa (JP);
Tomomi Oku, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 688 days.

(21) Appl. No.: 13/499,013

(22) PCT Filed: Sep. 30, 2010

(86) PCT No.: PCT/JP2010/005905
§ 371 (c)(1),
(2), (4) Date: Jun. 6, 2012

(87) PCT Pub. No.: WO2011/040042
PCT Pub. Date: Apr. 7, 2011

(65) Prior Publication Data
US 2012/0245548 A1    Sep. 27, 2012

(30) Foreign Application Priority Data
Sep. 30, 2009  (JP) .................... 2009-229091

(51) Int. Cl.
*A61F 13/15* (2006.01)
*A61F 13/20* (2006.01)
*A61F 13/56* (2006.01)
*A61F 13/58* (2006.01)

(52) U.S. Cl.
CPC ....... *A61F 13/15756* (2013.01); *A61F 13/5622* (2013.01); *A61F 13/58* (2013.01)

(58) Field of Classification Search
CPC  A61F 13/15756; A61F 13/5622; A61F 13/58
USPC .......... 604/385.01, 385.03, 385.31, 386–387, 604/392
See application file for complete search history.

(56) References Cited

U.S. PATENT DOCUMENTS 3,930,501 A * 1/1976 Schaar ...................... 604/365
4,850,992 A    7/1989 Amaral et al.
(Continued)

FOREIGN PATENT DOCUMENTS

| CN | 1366872 A | 9/2002 |
| JP | 9505227 A | 5/1997 |

(Continued)

OTHER PUBLICATIONS

Office Action mailed Jul. 25, 2013 corresponds to Chinese patent application No. 201080054276.8.
(Continued)

*Primary Examiner* — Michele M Kidwell
(74) *Attorney, Agent, or Firm* — Hauptman Ham, LLP

(57) ABSTRACT

A disposable diaper includes a side flap and a tape fastener. The tape fastener includes a tape attaching part attached to the side flap and exposed at an outer side face of the side flap. The side flap includes a leg periphery side region positioned closer to a leg of a wearer than the tape attaching part. The leg periphery side region is foldable upwardly to cover at least partially an end portion of the tape attaching part adjacent the leg of the wearer in response to a stress generated when the tape fastener is engaged, while being pulled, with the other end portion of the inner part in the longitudinal direction.

17 Claims, 11 Drawing Sheets

(56) References Cited

U.S. PATENT DOCUMENTS

| | | | |
|---|---|---|---|
| 5,106,385 A * | 4/1992 | Allen et al. | 604/391 |
| 5,899,895 A | 5/1999 | Robles et al. | |
| 6,692,475 B2 | 2/2004 | Mishima | |
| 7,033,341 B2 | 4/2006 | Mishima | |
| 7,198,622 B2 * | 4/2007 | Dahlgren | 604/386 |
| 2002/0062118 A1 * | 5/2002 | Almberg et al. | 604/392 |

FOREIGN PATENT DOCUMENTS

| | | | |
|---|---|---|---|
| JP | 2000126231 A | 5/2000 | |
| JP | 2005515839 A | 6/2005 | |
| WO | 03063749 A1 | 8/2003 | |
| WO | 2007034349 A1 | 3/2007 | |
| WO | 2008096505 A1 | 8/2008 | |

OTHER PUBLICATIONS

Office Action issued Feb. 7, 2014, corresponds to Eurasian patent application No. 201200385/31.
Office Action issued Jun. 25, 2014, corresponds to Egyptian patent application No. 2012030585.
International Search Report and Written opinion for PCT/JP2010/005905 dated Dec. 14, 2010.
Extended European Search Report issued May 2, 2014, corresponds to European patent application No. 10820163.3.
Office Action issued Jan. 6, 2015, corresponding to Australian patent application No. 2010302086.
Office Action issued Mar. 11, 2015, corresponding to Egyptian patent application No. 585/2012.
Office Action mailed May 8, 2015, corresponding to Philippines patent application No. 1/2012/500664.

* cited by examiner

DISPOSABLE DIAPER WITH GATHER INCLUDING ELONGATED STRETCHABLE MEMBERS

RELATED APPLICATIONS

The present application is a National Phase of International Application Number PCT/JP2010/005905, filed Sep. 30, 2010, and claims priority from Japanese Application Number 2009-229091, filed Sep. 30, 2009.

TECHNICAL FIELD

The present disclosure relates to an open-type disposable diaper.

BACKGROUND ART

Open-type disposable diapers have been widely used for infants and the like. In such a disposable diaper, a back-side part and an abdominal-side part are attached with each other using tape fasteners, such as hook-and-loop fasteners. Generally, an open-type disposable diaper includes an inner part having an absorber which absorbs excreta from a wearer, a pair of side flaps which are continuously connected with both side end portions of the inner part, respectively. Tape fasteners are respectively attached to side end portions of the side flaps to project outward in the width direction of the disposable diaper.

Japanese Patent Application Publication No. 2000-126231 discloses an open-type disposable diaper with a side flap having a curved outer rim at a leg periphery portion so as to fit to the shape of the leg of a wearer.

SUMMARY OF INVENTION

In an aspect, a disposable diaper comprises an inner part, a side flap, and a tape fastener. The inner part has a longitudinal direction and a width direction orthogonal to the longitudinal direction and includes a liquid permeable top sheet, a liquid impermeable back sheet, and an absorber provided between the top sheet and the back sheet. The side flap is at one of end portions of the inner part in the longitudinal direction and is connected to at least one of end portions of the inner part in the width direction. The tape fastener is attached to a side end portion of the side flap for engaging with the other end portion of the inner part in the longitudinal direction. The tape fastener includes a tape attaching part attached to the side flap and exposed at an outer side face of the side flap. The side flap includes a leg periphery side region positioned closer to a leg of a wearer than the tape attaching part when the disposable diaper is fitted onto the wearer. The leg periphery side region is configured to be folded upwardly to cover at least partially an end portion of the tape attaching part adjacent the leg of the wearer in response to a stress generated when the tape fastener is engaged, while being pulled, with the other end portion of the inner part in the longitudinal direction. The leg periphery side region folded upwardly prevents the end portion of the tape attaching part from directly contacting the wearer's skin.

In another aspect, a disposable diaper comprises an inner part, a side flap, and a tape fastener. The inner part has a longitudinal direction and a width direction orthogonal to the longitudinal direction and includes a liquid permeable top sheet, a liquid impermeable back sheet, and an absorber provided between the top sheet and the back sheet. The side flap is at one of end portions of the inner part in the longitudinal direction and is connected to at least one of end portions of the inner part in the width direction. The tape fastener is attached to a side end portion of the side flap for engaging with the other end portion of the inner part in the longitudinal direction. The tape fastener includes a tape attaching part attached to the side flap and exposed at an outer side face of the side flap. The side flap includes a leg periphery side region positioned closer to a leg of a wearer than the tape attaching part when the disposable diaper is fitted onto the wearer. The side flap has a flexural rigidity lower than that of the tape fastener and in a KB value range from about 0.1 to about 1 gf, such that the leg periphery side region is foldable upwardly along a folding line to cover at least partially the lower end portion of the tape attaching part to prevent the lower end portion of the tape attaching part from directly contacting the wearer's skin. The folding line extends obliquely upwardly from a boundary between the inner part and the side flap to a lower end portion of the tape attaching part, In a further aspect, a disposable diaper comprises an inner part, a side flap, and a pair of tape fasteners. The inner part has a longitudinal direction and a width direction orthogonal to the longitudinal direction and includes a liquid permeable top sheet, a liquid impermeable back sheet, and an absorber provided between the top sheet and the back sheet. The side flap is at one of end portions of the inner part in the longitudinal direction and is connected to both end portions of the inner part in the width direction. Each tape fastener includes a tape attaching part attached to an outer side face of the side flap and is engageable with the other end portion of the inner part in the longitudinal direction to define a waist hole and a pair of leg holes. The side flap includes leg periphery side regions each being arranged to project into the respective leg hole. Thus, the leg periphery side region is to be folded upwardly upon direct contact with a wearer's leg in use, and to cover at least partially the respective tape attaching part to prevent the tape attaching part from directly contacting the wearer's skin.

BRIEF DESCRIPTION OF DRAWINGS

FIG. 1 is a developed plan view of a disposable diaper in accordance with one or more embodiments;

[FIG. 2]

FIG. 3 is a perspective view of a wearer wearing the disposable diaper;

FIG. 4 is a partial, enlarged plan view of a back-side side flap portion of the disposable diaper;

FIG. 5 is a schematic view of various manufacturing steps of the disposable diaper;

[FIG. 6]

FIG. 7 is a view similar to FIG. 4 and showing a modification of an attaching position of the back-side side flap;

FIG. 8 is a view similar to FIG. 4 and showing another modification of the back-side side flap;

FIG. 9 is a view similar to FIG. 1 and showing a modification as to a shape of the side flap(s) of the disposable diaper;

FIG. 10 is a view similar to FIG. 4 and showing another modification as to the shape of the side flap; and

FIG. 11 is a view similar to FIG. 4 and showing still another modification as to the shape of the side flap.

DESCRIPTION OF EMBODIMENTS

Figure 1:
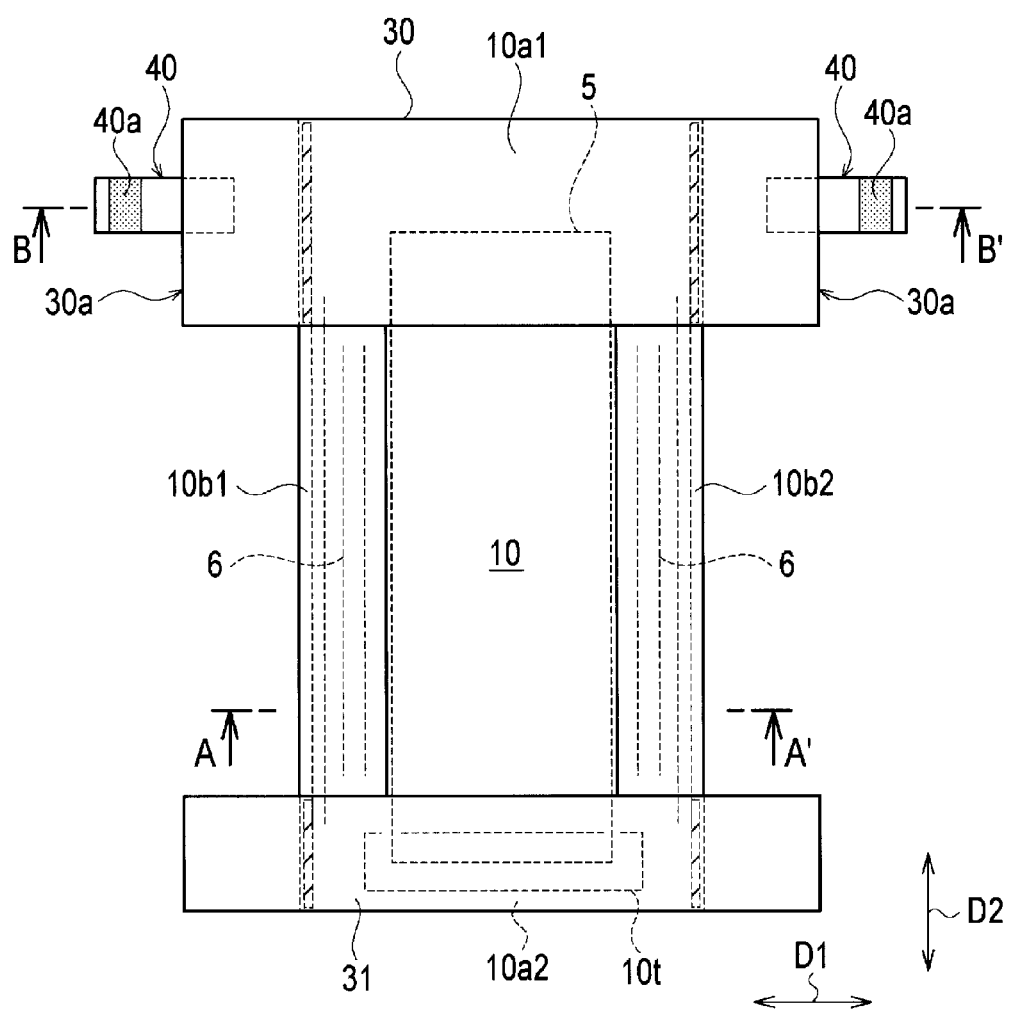
[FIG. 1]

The following is the inventors' observation regarding the known disposable diaper. Specifically, if the tape fasteners are exposed outside when a wearer wears the known disposable diaper, the tape fasteners formed of relatively hard materials may come into direct contact with the leg(s) of the wearer, causing discomfort or unpleasant feeling.

Such a problem can be solved of course by employing the structure in which a portion of each of the tape fasteners that may come into contact with the wearer's leg(s) is covered with a member formed of materials softer than the other portions of the tape fasteners. However, this solution increases the manufacturing cost.

A disposable diaper according to one or more embodiments of the present invention will be described below with reference to the drawings. In the descriptions of the following drawings, the same or similar reference numerals are given to the same or similar elements/portions. In addition, it should be noted that the drawings are schematic and are not to scale unless otherwise specified. Moreover, the drawings do not necessarily reflect the real life dimensional relationships and ratios of components.

Disposable Diaper Structure

Figure 2A:
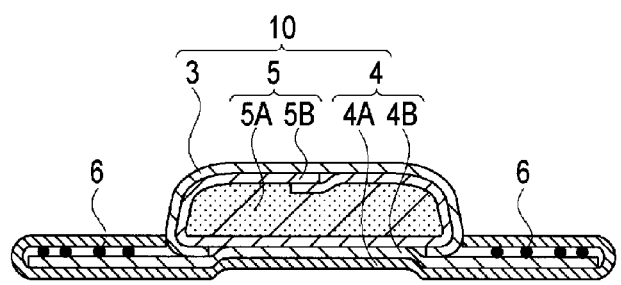
FIG. 2(a) is a cross-sectional view taken along the line A-A' in FIG. 1.

A disposable diaper 1 according to an embodiment of the present invention will be described by using FIGS. 1 and 2. FIG. 1 is a developed plan view of the disposable diaper 1. FIG. 2(a) is a cross-sectional view taken along the line A-A' of the disposable diaper 1 in FIG. 1, and FIG. 2(b) is a cross-sectional view taken along the line B-B' of the disposable diaper 1 in FIG. 1.

Figure 2B:
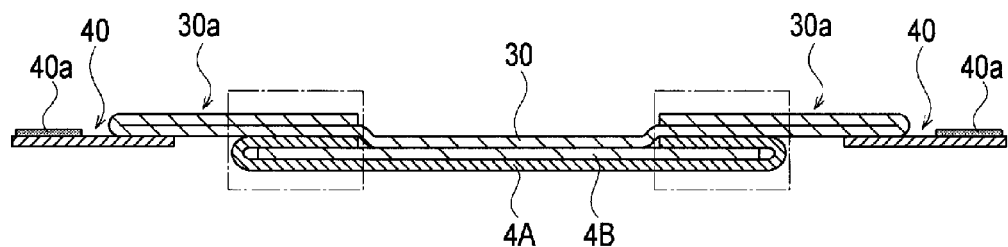
FIG. 2(b) is a cross-sectional view taken along the line B-B' in FIG. 1.

As shown in FIG. 1 and FIGS. 2(a) and 2(b), the disposable diaper 1 according to this embodiment is an open-type disposable diaper for infants or toddlers.

The disposable diaper 1 includes an inner part 10, a back-side side flap 30, and an abdominal-side side flap 31.

The inner part 10 has a longitudinal direction D2 and a width direction D1 orthogonal to the longitudinal direction in the developed plan view of FIG. 1. the inner part 10 is formed of a top sheet 3, a back sheet 4, and an absorber 5. Gathers 6 are provided in end portions 10b1 and 10b2 of the inner part 10 in the width direction D1. Tape fasteners 40 are respectively provided on side end portions 30a of the back-side side flap 30.

Figure 3:
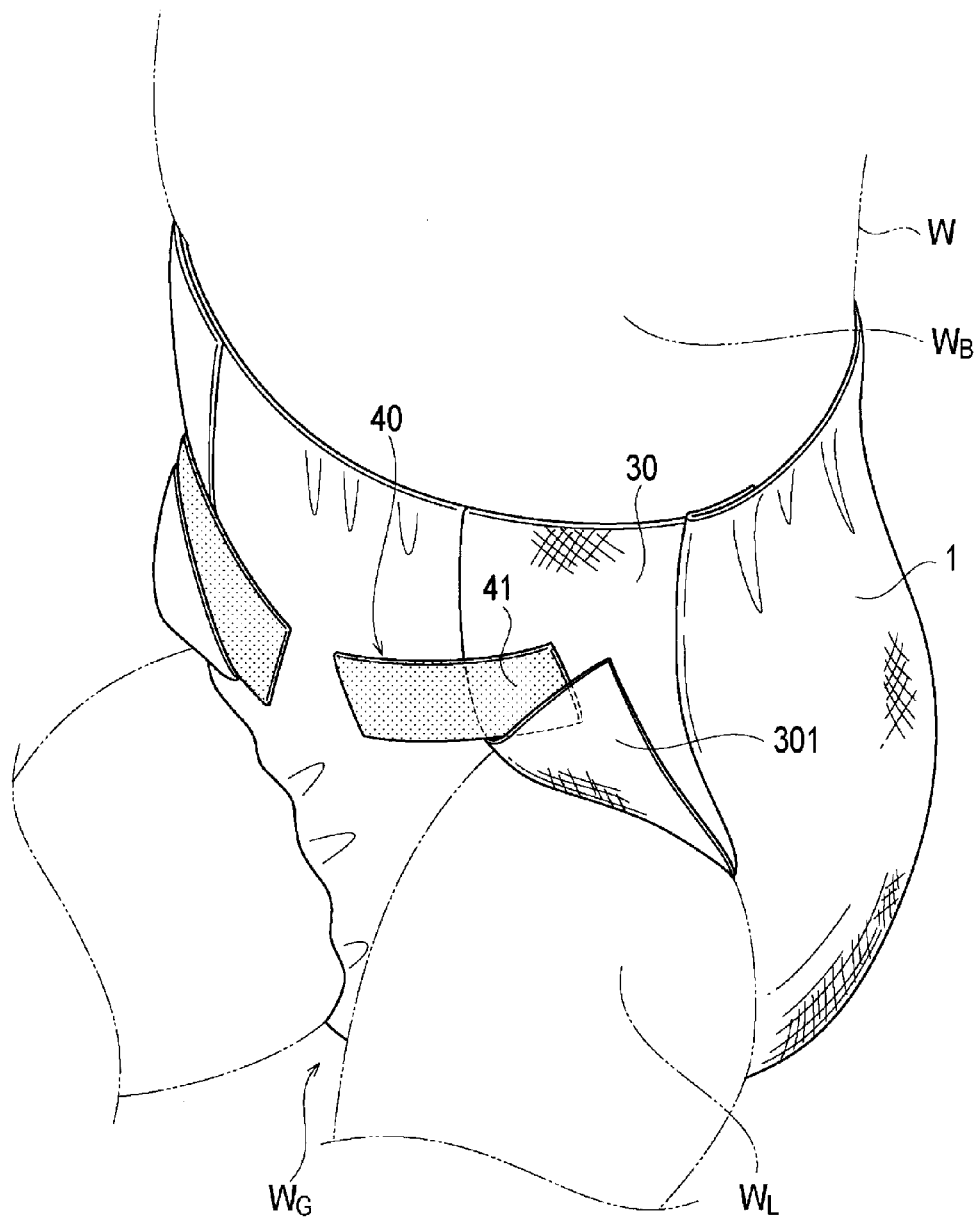
[FIG. 3]

The top sheet 3 is positioned at a skin-facing side of the disposable diaper 1 and can come into contact with the skin of a wearer W (not shown in FIGS. 1 and 2, see FIG. 3). The top sheet 3 wraps the absorber 5 therein. The top sheet 3 is formed of a liquid permeable sheet, such as a hydrophilic nonwoven fabric or textile, an apertured plastic film, or an apertured hydrophobic nonwoven fabric.

The back sheet 4 is provided at the opposite side of the top sheet 3 with the absorber 5 interposed therebetween. In other words, the back sheet 4 is positioned on a garment-facing side when the wearer W wears the disposable diaper 1. The back sheet 4 includes a nonwoven fabric 4A which can come into contact with the clothing (garment) of the wearer W, and a back film 4B positioned inward of the nonwoven fabric 4A (i.e., on the skin-facing side). The nonwoven fabric 4A and the back film 4B are bonded by HMA (hot melt adhesive) or the like.

As shown in FIG. 2(b), the nonwoven fabric 4A is folded up so as to cover the back film 4B, and the back-side side flap 30 is stacked thereon. The back-side side flap 30 is folded up to be doubled at portions to which the tape fasteners 40 are attached. A part of the side end portion 30a of the folded back-side side flap 30 overlaps the region where the nonwoven fabric 4A is folded up. Accordingly, a region where multiple sheet-like members are stacked one on top the other (inside the dotted frame in FIG. 2(b)) is formed. In this manner, the sheet-like members are hard to break, and tensile stress generated when the disposable diaper 1 is fitted onto the wearer W can be reliably transmitted from the tape fasteners 40 to the back-side side flap 30, even if the back-side side flap 30 and the tape fasteners 40 are pulled to the outside in the width direction.

Examples of materials for the nonwoven fabric 4A include hydrophobic nonwoven fabrics such as a spunbond-melt blown-spunbond (SMS) nonwoven fabric, a spunbond (SB) nonwoven fabric, and a point bond nonwoven fabric. Examples of materials for the back film 4B include a moisture-permeable or moisture-impermeable film.

The absorber 5 is provided between the top sheet 3 and the back sheet 4, and absorbs the excreta (urine or the like) that the wearer W discharged. The absorber 5 has an absorbent core 5A which absorbs liquid and an absorptive sheet 5B. The absorbent core 5A is wrapped with the absorptive sheet 5B. The absorbent core 5A is bonded to the back sheet 4 by HMA or the like in a state being wrapped with the top sheet 3.

The absorbent core 5A contains a hydrophilic fiber. Examples of materials for such a hydrophilic fiber include milled pulp, cellulose such as cotton, regenerated cellulose such as rayon and fibril rayon, semisynthetic cellulose such as acetate and triacetate, a particulate polymer, a fibrous polymer, a thermoplastic hydrophobic chemical fiber, a hydrophilically-treated thermoplastic hydrophobic chemical fiber, or the like or any mixture thereof. On the other hand, tissue can be used as the absorptive sheet 5B.

The gather 6 is a sheet-like member formed of a hydrophobic (water-repellent) nonwoven fabric. The gather 6 contains multiple elongated stretchable members (e.g., polyurethane fibers, such as those available under the registered trademark Lycra), and has stretchability. The gathers 6 are provided in the end portions 10b1 and 10b2 in the width direction D1 of the inner part 10. The gathers 6 extend in the longitudinal direction D2 of the inner part 10. Accordingly, when the disposable diaper 1 is fitted onto the wearer W, the gathers 6 or the end portions 10b1 and 10b2 of the inner part 10 rise upward from the absorber 5 along the body shape of the wearer W, thereby surely preventing the excreta from the wearer W from leaking to the outside.

The back-side side flap 30 is continuously connected with an end portion 10a1 of the inner part 10 in the longitudinal direction D2. In other words, the back-side side flap 30 extends across an entire width of the inner part 10. Specifically, the back-side side flap 30 is continuously connected with the end portions 10b1 and 10b2 of the inner part 10 in the width direction D1, at the end portion 10a1. In the specifically illustrated configuration of this embodiment, the back-side side flap 30 has a rectangular shape.

The back-side side flap 30 is formed of a liquid impermeable nonwoven fabric. In a specific configuration of this embodiment, the back-side side flap 30 is formed of an SMS nonwoven fabric. In another specific configuration of this embodiment, an SB nonwoven fabric or the like is used for the back-side side flap 30 instead of the SMS nonwoven fabric. The abdominal-side side flap 31 in a specific configuration of this embodiment is formed of the same nonwoven fabric as that of the back-side side flap 30. As will be apparent from the manufacturing process described below, the side flap 30 is defined by a liquid-impermeable sheet other than the back sheet 4 and is directly attached to an inner side face (skin-facing side) of the end portion 10a1 of the inner part 10 in the longitudinal direction D2 to be in direct contact with the wearer W, in use.

The tape fasteners 40 are attached to the side end portions 30a of the back-side side flap 30 by HMA or the like, and for engaging the end portion 10a1 (back-side part) with the end portion 10a2 (abdominal-side part) of the inner part 10 to define a waist hole for the waistline of the wearer W, and a pair of leg holes for the legs of the wearer W. The tape fasteners 40 are made of materials harder than the back-side side flap 30.

Specifically, each of the tape fasteners 40 in a specific configuration of this embodiment includes a male member of a so-called hook-and-loop fastener, that is, an engaging face 40a having multiple hook-shaped projection groups (hooks). The engaging face 40a engages with a target tape portion 10t provided on the end portion 10a2 of the inner part 10. In a specific configuration of this embodiment, a part, except the engaging face 40a, of the tape fastener 40 is formed of an SB nonwoven fabric. In another specific configuration of this embodiment, a resin film or the like is used for the tape fastener 40 instead of the SB nonwoven fabric.

FIG. 3 shows a state where the wearer W wears the disposable diaper 1. As shown in FIG. 3, the disposable diaper 1 is fitted onto the wearer W in such a manner that the absorber 5 (see FIGS. 1 and 2) may be positioned to a groin $W_G$ of the wearer W.

To fit the disposable diaper 1 onto the wearer W, a care taker (not shown) pulls the tape fasteners 40 to the abdominal side of the wearer W, and engages the pulled tape fasteners 40 with the end portion 10a2 of the inner part 10. In this manner, the disposable diaper 1 is surely fitted onto the wearer W without being displaced, even if the wearer W moves.

When the disposable diaper 1 is fitted onto the wearer W, since each of the tape fasteners 40 is pulled and then engaged with the target tape portion 10t provided in the end portion 10a2 of the inner part 10, a stress (tensile stress) is generated and transmitted from the tape fasteners 40 to the back-side side flap 30. As a result, a leg periphery side region 301 of the back-side side flap 30 is folded onto the tape fastener 40 in response to the stress and covers an end portion 41a (not shown in FIG. 3, see FIG. 4), of a tape attaching part 41 of the tape fastener 40. The end portion 41a is a lower end portion of the tape attaching part 41 and is adjacent a leg $W_L$ of the wearer W in use. Accordingly, the end portion 41a of the tape attaching part 41 does not come into direct contact with the skin of the wearer W. The mechanism in which the leg periphery side region 301 is folded onto the tape fastener 40 will be described later.

Figure 4:
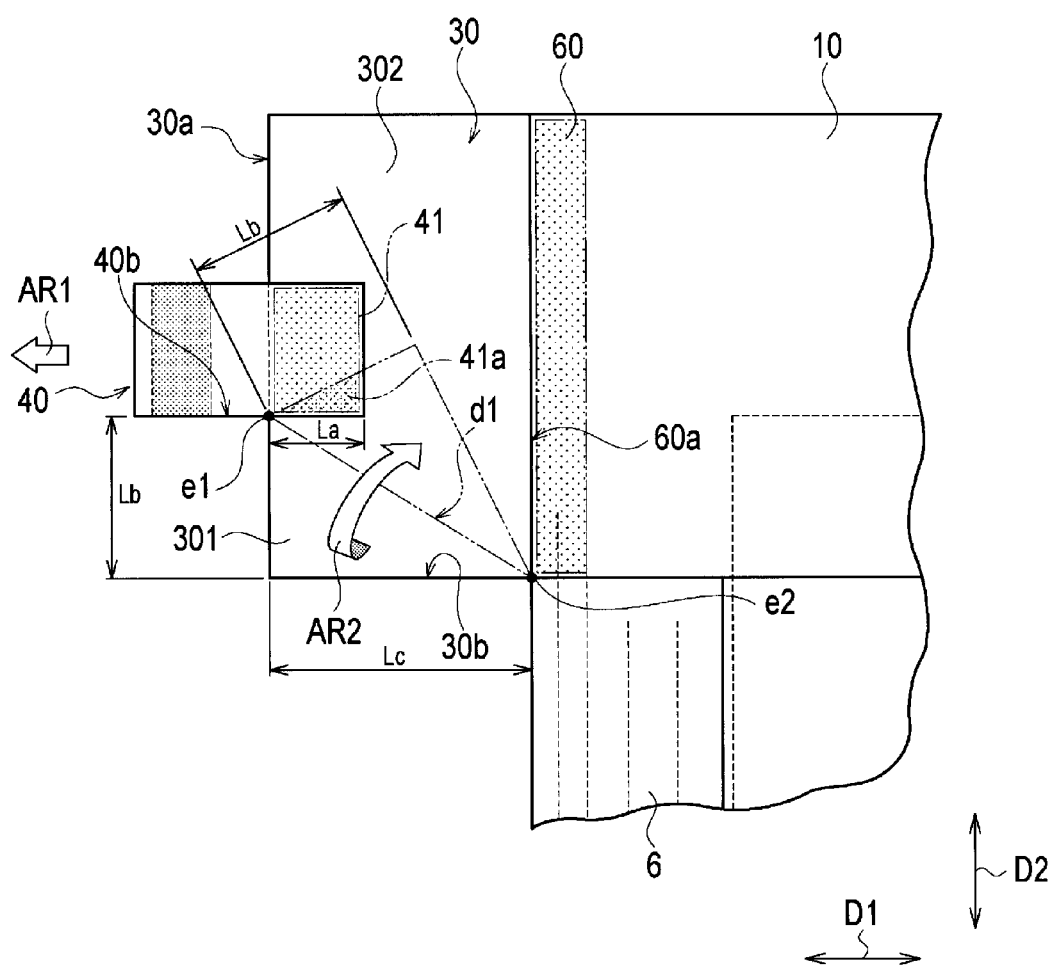
[FIG. 4]

Next, with reference to FIG. 4, the back-side side flap 30, the leg periphery side region 301 of the back-side side flap 30, and the tape fastener 40 will be described in detail. FIG. 4 is a partial, enlarged plan view of the back-side side flap 30 portion.

The back-side side flap 30 has a bonded part 60 which is bonded to the inner part 10. Specifically, the back-side side flap 30 is bonded to the skin-facing side (inner side face) of the inner part 10 using the HMA or the like.

The tape fastener 40 has the tape attaching part 41 attached to the back-side side flap 30. The tape attaching part 41 is attached to the side end portion 30a of the back-side side flap 30 to be exposed at the garment-facing side (outer side face) of the back-side side flap 30. In the specifically illustrated configuration, the tape attaching part 41 is attached to the center portion of the back-side side flap 30 in the longitudinal direction D2 of the inner part 10.

The back-side side flap 30 has the leg periphery side region 301 positioned closer to the end portion 10a2 (not shown in FIG. 4, see FIG. 1) than the tape attaching part 41, and a body side region 302 positioned closer to the end portion 10a1 than the tape attaching part 41.

When the disposable diaper 1 is fitted onto the wearer W, the leg periphery side region 301 is positioned closer to the leg $W_L$ of the wearer W than the tape attaching part 41. Similarly, at the time of fitting, the body side region 302 is positioned closer to a body $W_B$ (waistline) of the wearer W than the tape attaching part 41. Note that, the time of fitting the disposable diaper 1 onto the wearer W means the state when the disposable diaper 1 is applied to the wearer W and before the tape fastener 40 engages with the target tape portion 10t, that is, before the leg periphery side region 301 is folded onto the tape fastener 40.

As mentioned above, when the disposable diaper 1 is fitted onto the wearer W, the leg periphery side region 301 is folded upwardly (FIG. 3) and covers at least partially the end portion 41a of the tape attaching part 41. In the back-side side flap 30, a length of the tape attaching part 41 in the width direction D1 of the inner part 10 is La, a length of the leg periphery side region 301 in the longitudinal direction D2 of the inner part 10 is Lb, and a length from the side end portion 30a of the back-side side flap 30 to a boundary between the inner part 10 and the back-side side flap 30 is Lc. In a specific configuration of this embodiment, La, Lb, and Lc satisfy the relationship of La<Lb<Lc.

Specifically, the leg periphery side region 301 is folded (see, arrow AR2 in FIG. 4) onto the tape fasteners 40 along the line (a folding line d1) connecting a point e1 where a lower end portion 40b of the tape fasteners 40 intersects with the side end portion 30a of the back-side side flap 30 to a point e2 where an end portion 60a, at the outer side in the width direction D1, of the bonded part 60 intersects with a lower end portion 30b of the back-side side flap 30. Since Lb is longer than La, the leg periphery side region 301 folded onto the tape fastener 40 can cover the end portion 41a of the tape attaching part 41 adjacent the leg $W_L$. Furthermore, since Lc is longer than La and Lb, and the point e2 is positioned closer to the leg $W_L$ than the point e1, the leg periphery side region 301 can surely cover the end portion 41a, even when being folded along the folding line d1 inclined to the extending direction (the width direction D1) of the end portion 41a or the lower end portion 30b.

In a specific configuration of this embodiment, a SMS non-woven fabric having a mass per unit area (basic weight) of 13 $g/m^2$ is used to formed the back-side side flap 30. In the side end portions 30a where the tape fastener 40 is attached to the back-side side flap 30, the SMS non-woven fabric is doubled as discussed with respect to FIG. 2(b). As a result, the total mass per unit area of the SMS nonwoven fabric (a second material) which constitutes the side end portions 30a of the back-side side flap 30 is 26 $g/m^2$ (the SMS non-woven fabric of 13 $g/m^2$ is doubled). The mass per unit area of a SB nonwoven fabric (a first material) which constitutes the tape fasteners 40 is 80 $g/m^2$. In other words, the mass per unit area of the side end portion 30a where the tape fastener 40 is attached to the back-side side flap 30 is smaller than the mass per unit area of the tape fasteners 40.

Accordingly, the back-side side flap 30 as a whole, and the side end portions 30a where the tape fastener 40 is attached to the back-side side flap 30 in particular, is softer than the tape fastener 40. Specifically, the flexural rigidity of the SMS nonwoven fabric which constitutes the back-side side flap 30 (second flexural rigidity) is smaller than the flexural rigidity (first flexural rigidity) of the SB nonwoven fabric which constitutes the tape fastener 40. The flexural rigidity (KB) will be described later.

Disposable Diaper Manufacturing Method

Next, a manufacturing method of the disposable diaper 1 will be described with reference to FIG. 5. The manufacturing method of the back-side side flap 30 and abdominal-side side flap 31 will be mainly described herein. Other parts, such as the inner part 10, can be manufactured in accordance with known manufacturing methods.

Figure 5:
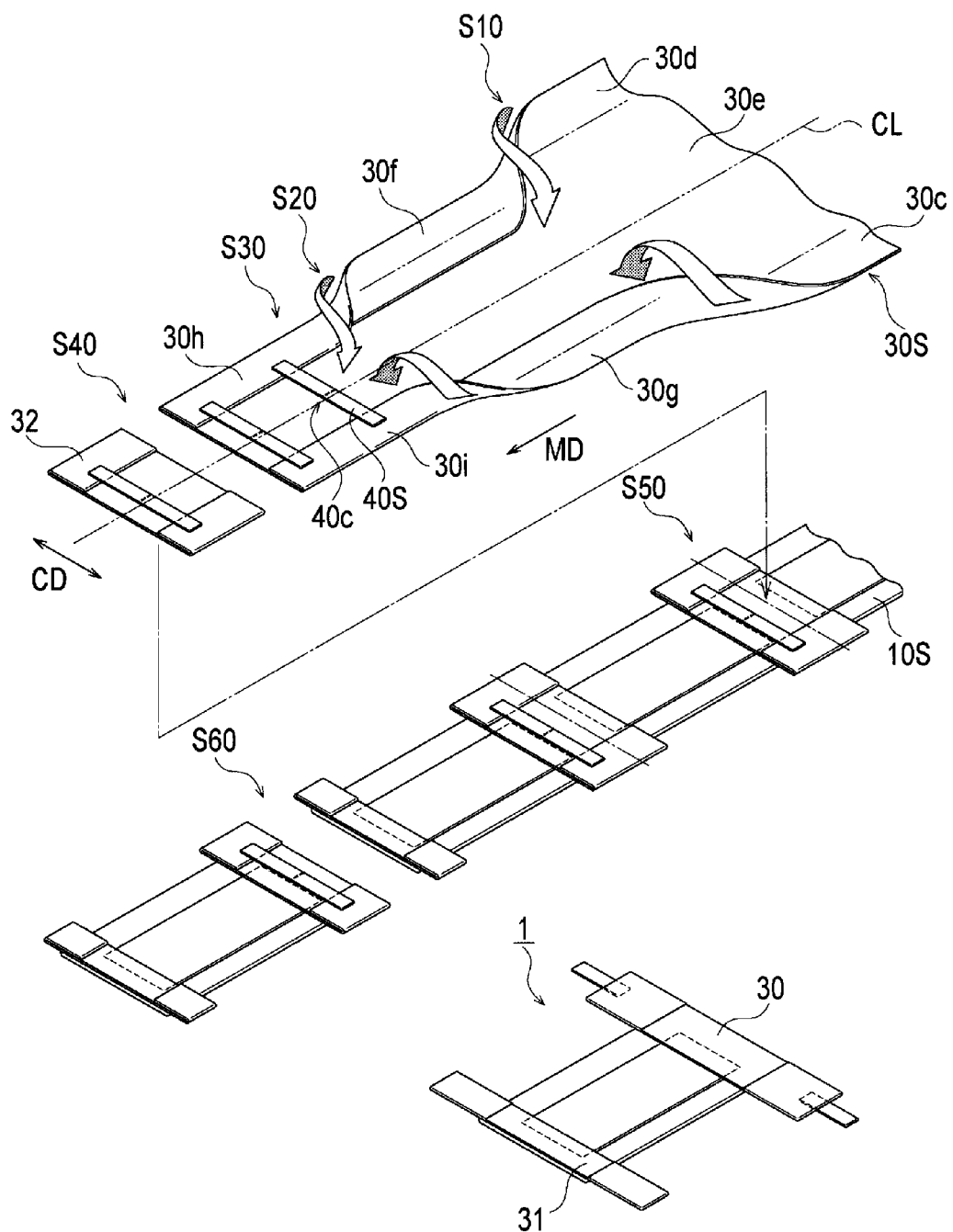
[FIG. 5]

FIG. 5 schematically shows various manufacturing steps of the disposable diaper 1. As shown in FIG. 5, the manufacturing step of the disposable diaper 1 includes a first folding step S10, a second folding step S20, a tape fastener attaching step S30, a first cutting step S40, a side flap attaching step S50, and a second cutting step S60.

At the first folding step S10, both-side end portions 30c and 30d of a continuous flap sheet 30S which is continuous in a conveyance direction (machine direction) MD are folded onto a top face 30e of the flap sheet 30S toward a center line CL of the flap sheet 30S, and are bonded to the top face 30e by the HMA or the like. The center line CL is a straight line which passes through the center of the flap sheet 30S in the width direction (the cross direction CD which is perpendicular to the conveyance direction MD) thereof.

At the second folding step S20, folded end portions 30f and 30g obtained after the first folding step S10 are further folded onto the top face 30e of the flap sheet 30S toward the center line CL of the flap sheet 30S. In this manner, overlapped portions 30h and 30i where multiple layers of the flap sheets 30S are stacked one on top the other are formed at the both end portions of the flap sheet 30S. The overlapped portions 30h and 30i constitute the side end portion 30a (see FIG. 4) of the back-side side flap 30. The overlapped portions 30h and 30i formed at the second folding step S20 are not bonded to the flap sheet 30S.

At the tape fastener attaching step S30, a tape member 40S which is an integral member comprising a pair of the tape fasteners 40 is attached on the flap sheet 30S at predetermined intervals in the conveyance direction MD. The center portion of the tape member 40S is processed to include perforations 40c in the conveyance direction MD, for example, to easily separate the tape member 40S into two tape fasteners 40.

At the first cutting step S40, the flap sheet 30S is cut at predetermined intervals in the cross direction CD. Cut pieces 32 obtained by cutting the flap sheet 30S are each have one back-side side flap 30 and one abdominal-side side flap 31 integrated with each other.

At the side flap attaching step S50, the cut pieces 32 are arranged on a continuous inner part body 10S at predetermined intervals. The inner part body 10S includes a continuous body of the back sheet 4 with the absorber 5 (wrapped with the topsheet 3) arranged intermittently thereon. The cut pieces 32 are arranged on the inner part body 10S so as to respectively cover spaces between the adjacent absorbers 5, and are bonded to the inner part body 10S.

At the second cutting step S60, the inner part body 10S to which the cut pieces 32 have been bonded is cut in the cross direction CD. Each of the cut pieces 32 is divided into the back-side side flap 30 of one diaper and the abdominal-side side flap 31 of another diaper, thereby completing the disposable diaper 1.

Side Flap Materials

Next, a material (e.g., nonwoven fabric) that constitutes a side flap, specifically the back-side side flap 30, in a specific configuration of this embodiment will be described. As mentioned above, an SMS nonwoven fabric and an SB nonwoven fabric can be used as the back-side side flap 30.

Here, a test method to determine characteristics of a material suitable for the back-side side flap 30, and a result thereof will be described. In the test method, (1) the flexural rigidity of various materials was evaluated by using a measuring device (hereinafter, test 1), and (2) the folded state of the side flap after the wearer W had worn a disposable diaper for 30 minutes and the material tolerance after the wearer W had worn the disposable diaper (hereinafter, test 2) were evaluated.

The disposable diapers formed of materials in Examples 1 to 3 and Comparative Examples 1 and 2 shown in Table 1 were used in the tests 1 and 2. Note that, the description (single layer or double layer) in the parenthesis of "type of side flap materials" indicates the presence of overlapping materials. For the double layer, the total mass per unit area of all layers of the whole materials is shown. The size (width) of each of the materials was 30 mm.

TABLE 1

| | TYPE OF SIDE FLAP MATERIALS | MASS PER UNIT AREA | FLEXURAL RIGIDITY (KB) UNIT: gf | FOLDABILITY | MATERIAL TOLERANCE |
|---|---|---|---|---|---|
| EXAMPLE 1 | SPUNBOND-MELT BLOWN-SPUNBOND NONWOVEN FABRIC (DOUBLE LAYER) | 26 g/m$^2$ | 0.1578 | 100% | OK |
| EXAMPLE 2 | SPUNBOND NONWOVEN FABRIC (SINGLE LAYER) | 30 g/m$^2$ | 0.3208 | 100% | OK |
| EXAMPLE 3 | SPUNBOND NONWOVEN FABRIC (DOUBLE LAYER) | 60 g/m$^2$ | 0.8335 | 50% | OK |
| COMPARATIVE EXAMPLE 1 | SPUNBOND-MELT BLOWN-SPUNBOND NONWOVEN FABRIC (SINGLE LAYER) | 13 g/m$^2$ | LESS THAN 0.01 | 100% | NG |
| COMPARATIVE EXAMPLE 2 | SPUNBOND NONWOVEN FABRIC (SINGLE LAYER) | 70 g/m$^2$ | 1.0136 | 0% | OK |

As shown in Table 1, Examples 1 to 3 were good with regard to the flexural rigidity, the foldability, and the material tolerance. Meanwhile, Comparative Example 1 had a lower mass per unit area than Examples 1-3, and the flexural rigidity of Comparative Example 1 could not be measured. Comparative Example 2 had a higher mass per unit area than Examples 1-3, and there was no problem in the material tolerance; however, there was a problem in the foldability.

In the test 1, the KES AUTO Pure Bending Tester (manufactured by KATO TECH CO., LTD.) was used, and a KB value which is a flexural rigidity in the vertical direction to the flat surface of materials was measured. K indicates a curvature (unit: cm$^{-1}$) and B indicates a folding moment (unit: gf·cm). In other words, the flexural rigidity shows the magnitude of the stress generated when a constant curvature is applied to the moment to bend a material per unit width.

Specifically, the KB value generated when a predetermined curvature (+−2.5 cm$^{-1}$) is applied to the material was measured. The KB value shown in Table 1 indicates the average of the five measured values. The measuring device cannot measure a KB value less than 0.01.

The KB value is preferably within the range from 0.1 or more to less than 1.0, based on the test result shown in Table 1. When general SB nonwoven fabric and SMS nonwoven fabric are used, if the KB value is less than 0.1, the rigidity of materials is too low and there is no sufficient strength. Thus, the back-side side flap 30 might be damaged, when the disposable diaper is fitted onto the wearer W. If the KB value is 1.0 or more, the rigidity of materials is too high. Thus, even when the tape fastener 40 is pulled, the back-side side flap 30 (the leg periphery side region 301) is not easily folded onto the tape fastener 40 along the folding line d1.

In the test 2, observations were made regarding the folded state of the side flap after each of the disposable diapers respectively using the materials of Examples 1 to 3 and Comparative Examples 1 and 2 had been worn by the wearer W for 30 minutes, and the material tolerance after each of the disposable diapers had been worn by the wearer W. The test 2 was carried out twice for each Example and each Comparative Example. In the test 2, an SB nonwoven fabric having the mass per unit area of 80 g/m$^2$ was used as the tape fastener 40. The KB value of the tape fastener 40 was 1.303.

The "foldability" evaluation indicates the presence or absence of folding of the back-side side flap 30 onto the tape fastener 40 after the disposable diaper had been fitted onto the wearer W for 30 minutes. "100%" under "foldability" indicates that the folding was observed in both tests. "50%" under "foldability" indicates that the folding was observed in only one test out of the two tests. "0%" under "foldability" indicates that the folding was not observed at all in the two tests.

The "material tolerance" evaluation indicates whether a trouble, such as a tear in the back-side side flap 30, occurred after the disposable diaper had been worn by the wearer W for 30 minutes. "OK" under "material tolerance" indicates that troubles, such as a tear, did not occur. On the other hand, "NG" under "material tolerance" indicates that troubles, such as a tear, occurred.

The mass per unit area of the back-side side flap 30 is preferably within the range from 20 g/m$^2$ to 60 g/m$^2$, and more preferably within the range from 25 g/m$^2$ to 40 g/m$^2$, based on the result of the tests 1 and 2. The mass per unit area of the tape fastener 40 is preferably between 50 g/m$^2$ and 80 g/m$^2$.

Although the masses per unit area of the back-side side flap 30 and the tape fastener 40 are preferably within the ranges mentioned above, respectively, however, the masses per unit area of the back-side side flap 30 and the tape fastener 40 are not necessarily limited to such ranges. For example, the mass per unit area of the tape fastener 40 may be between 40 g/m$^2$ and 120 g/m$^2$.

In some embodiments, the mass per unit area of the tape fastener 40 is preferably 1.5 times to 5 times the mass per unit area of the back-side side flap 30, and more preferably twice to 4 times.

In addition, the flexural rigidity (KB value) of the back-side side flap 30, especially in the side end portions 30a where the tape fastener 40 is attached to the back-side side flap 30, is preferably smaller than the flexural rigidity (KB value) of the tape fastener 40.

As described above, when the disposable diaper 1 is fitted onto the wearer W, the leg periphery side region 301 of the back-side side flap 30 is folded onto the tape fastener 40 due to the stress generated when the tape fastener 40 is engaged, while being pulled, with the end portion 10a2 (the target tape portion 10t) of the inner part 10. Accordingly, the leg periphery side region 301 covers the end portion 41a of the tape attaching part 41 that is adjacent the wearer's leg W$_L$. Specifically, as shown in FIG. 4, the tension that pulls the tape fastener 40 in the direction of the arrow AR1 generates the stress along the folding line d1 that connects the points e1 and e2, so that the leg periphery side region 301 of the back-side side flap 30 is folded onto the tape fastener 40, as shown by the arrow AR2.

Accordingly, the tape fastener 40 formed of the materials harder than that of the back-side side flap 30 does not come into direct contact with the leg W$_L$ of the wearer W, thereby avoiding discomfort or unpleasant feeling to the wearer W.

The tape fastener 40 has a simple configuration, that is, the tape fastener 40 is exposed at the outer side face of the back-side side flap 30. Thus, the manufacturing cost of the disposable diaper 1 can be reduced, in comparison with the configuration in which the end portion 41a of the tape fastener 40 which may come into contact with the leg W$_L$ of the wearer W is covered with a member formed of materials softer than that of the tape fastener 40.

In addition, when the disposable diaper 1 is fitted onto the wearer W, the end portion 41a of the tape fastener 40 is placed on the inguinal region of the wearer W at the point e1 as the starting point. Accordingly, the tape fastener 40 supports the heavy absorber 5 when the wearer W is standing up or is walking, so that the disposable diaper 1 can be prevented from being displaced.

According to a specific configuration of this embodiment, as shown in FIG. 4, La, Lb, and Lc satisfy the relationship of La<Lb<Lc. Accordingly, even when the back-side side flap 30 is folded along the folding line d1 which inclines relative to the width direction D1, the back-side side flap 30 can surely cover the end portion 41a of the tape attaching part 41 at the side of the leg W$_L$.

According to a specific configuration of this embodiment, the mass per unit area of the back-side side flap 30, especially in the side end portions 30a where the tape fastener 40 is attached to the back-side side flap 30, is smaller than that of the tape fastener 40. The flexural rigidity of the back-side side flap 30 is also smaller than the flexural rigidity of the tape fastener 40. In other words, the back-side side flap 30 is softer than the tape fastener 40 so as to be foldable easily along the folding line d1 to prevent the tape fastener 40 harder than the back-side side flap 30 from directly contacting the wearer W. In addition, the larger mass per unit area of the tape fastener 40 improves the strength of the tape fastener 40, and hence, it is easy to obtain the necessary strength for supporting the absorber 5 (which becomes heavier as it absorbs body discharge in use) and the sufficient strength against the pulling at the time of fitting the disposable diaper 1 on the wearer W.

In a specific configuration of this embodiment, the leg periphery side region 301 of the back-side side flap 30 projects into a leg hole of the diaper to be in direct contact with the wearer's leg W$_L$. Thus, the leg periphery side region 301 is easily folded upwardly due to direct contact with the wearer's leg W$_L$ in addition to the stress generated when the tape fasteners 40 are engaged with the other end portion 10a2 of the inner part 10.

Other Embodiments

As mentioned above, one or more exemplary embodiments of the present invention have been disclosed in detail. However, it should not be understood that the description and the drawings which constitute a part of this disclosure limit the present invention. Various alternative embodiments, examples, and operating techniques will be apparent to those ordinarily skilled in the art from this disclosure. For example, the disclosed embodiment(s) of the present invention can be modified at least as follows.

First Modification

FIGS. 6(a) to 6(e) show modifications of the back-side side flap 30. As shown in FIGS. 6(a) to 6(e), a high rigidity part P, which defines or contains one or more lines approximately coincident or parallel to the folding line d1 (see FIG. 4), is formed, e.g., by a heat-seal pattern processing or an emboss processing. Since the back-side side flap 30 is pressed by the pattern processing or the emboss processing, the high rigidity part P has rigidity higher than the other parts of the back-side side flap 30.

The high rigidity part P includes or defines a portion which extends obliquely from the end portion 41a of the tape attaching part 41 (specifically, the point e1) toward a boundary (specifically, the point e2) between the inner part 10 and the back-side side flap 30 (see FIG. 4). Such portion defines the folding line d1.

Figure 6A:
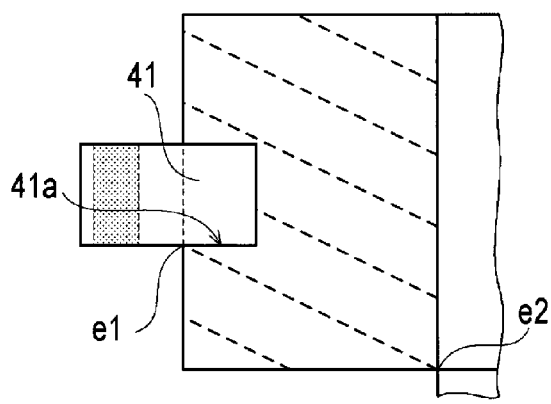
FIGS. 6(a) to (e) are various partial, enlarged plan views showing modifications of the back-side side flap.
Figure 6D:
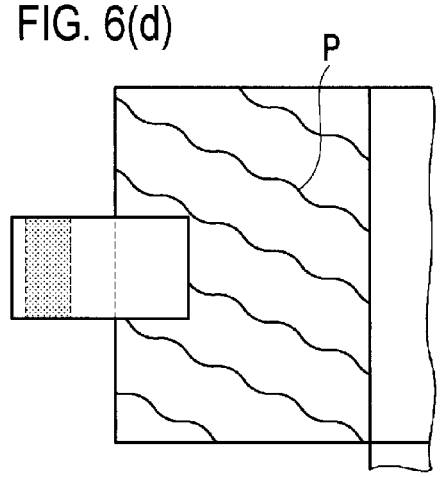
Figure 6B:
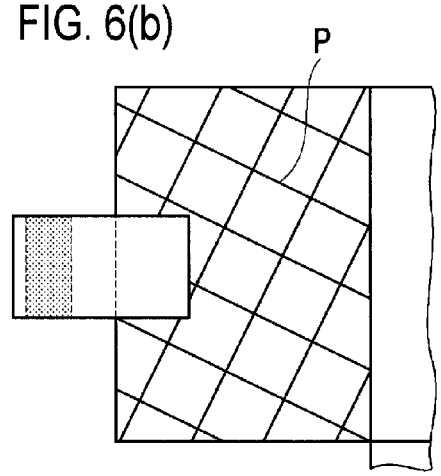
Figure 6E:
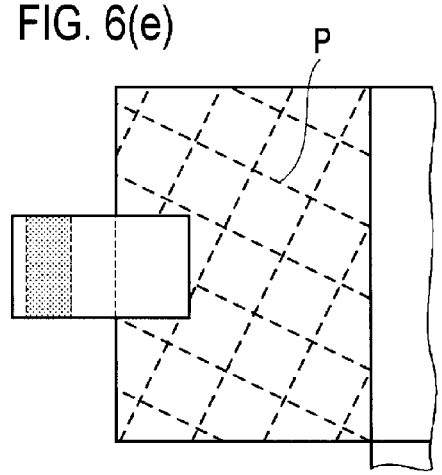
Figure 6C:
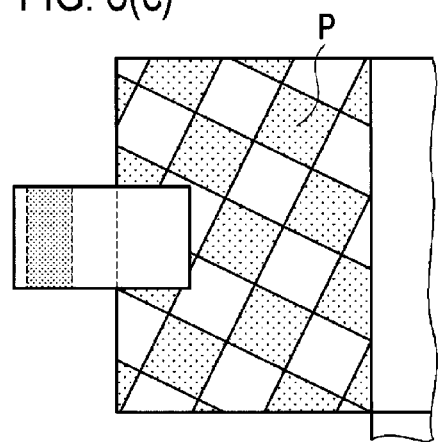

As shown in FIGS. 6(b), 6(c), and 6(e), at least a part of the high rigidity part P is additionally formed in a direction crossing (e.g., perpendicular to) the folding line d1. As shown in FIG. 6(d), the high rigidity part P need not be a straight line. Preferably, regions of different rigidities (e.g., the high rigidity part P and the other part of the back-side side flap 30) are alternatingly arranged to define the folding line d1 and/or a further folding line d2 (as will be described later).

According to the first modification, the back-side side flap 30 is foldable easily along the high rigidity part P onto the tape fastener 40.

Second Modification

Figure 7:
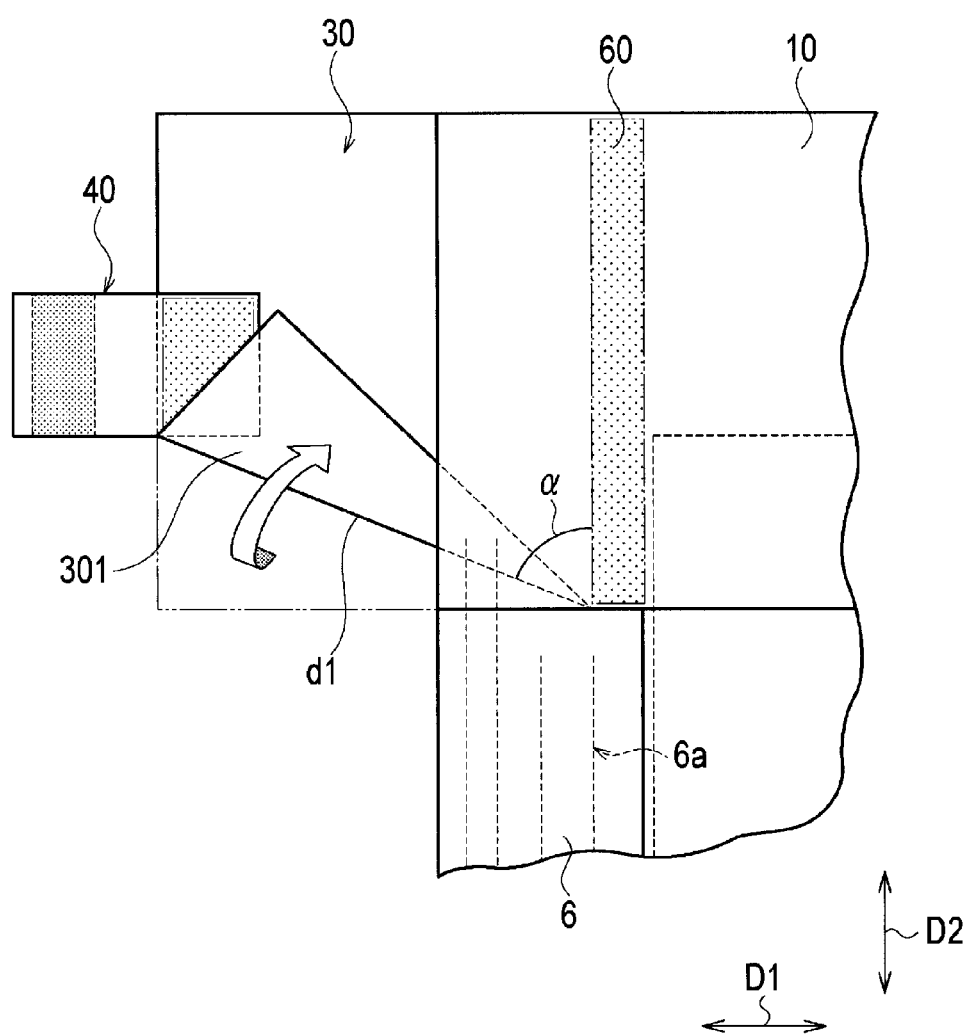
[FIG. 7]

FIG. 7 shows a modification in an attaching position of the back-side side flap 30. As shown in FIG. 7, the bonded part 60 of the back-side side flap 30 and the inner part 10 is formed closer to the center of the inner part 10 in the width direction D1 than an innermost stretchable member 6a of the gather 6. In other words, the bonded part 60 is, in the width direction, inboard of the innermost stretchable member 6a among the stretchable members of the gather 6.

According to the second modification, as an angle alpha made by the folding line d1 and a straight line along the outer edge of the bonded part 60 becomes large, the area of a portion (the leg periphery side region 301) of the back-side side flap 30 that is foldable onto the tape fastener 40 increases. Accordingly, the back-side side flap 30, when folded, can further surely cover the tape fastener 40. Further, since the bonded part 60 is formed closer to the center of the inner part 10 than the innermost stretchable member 6a of the gather 6, the gather 6 is easy to open outward with the assistance of the back-side side flap 30 when the tape fastener 40 is pulled. Therefore, the gather 6 may be easily fitted onto the wearer W appropriately.

Third Modification

Figure 8:
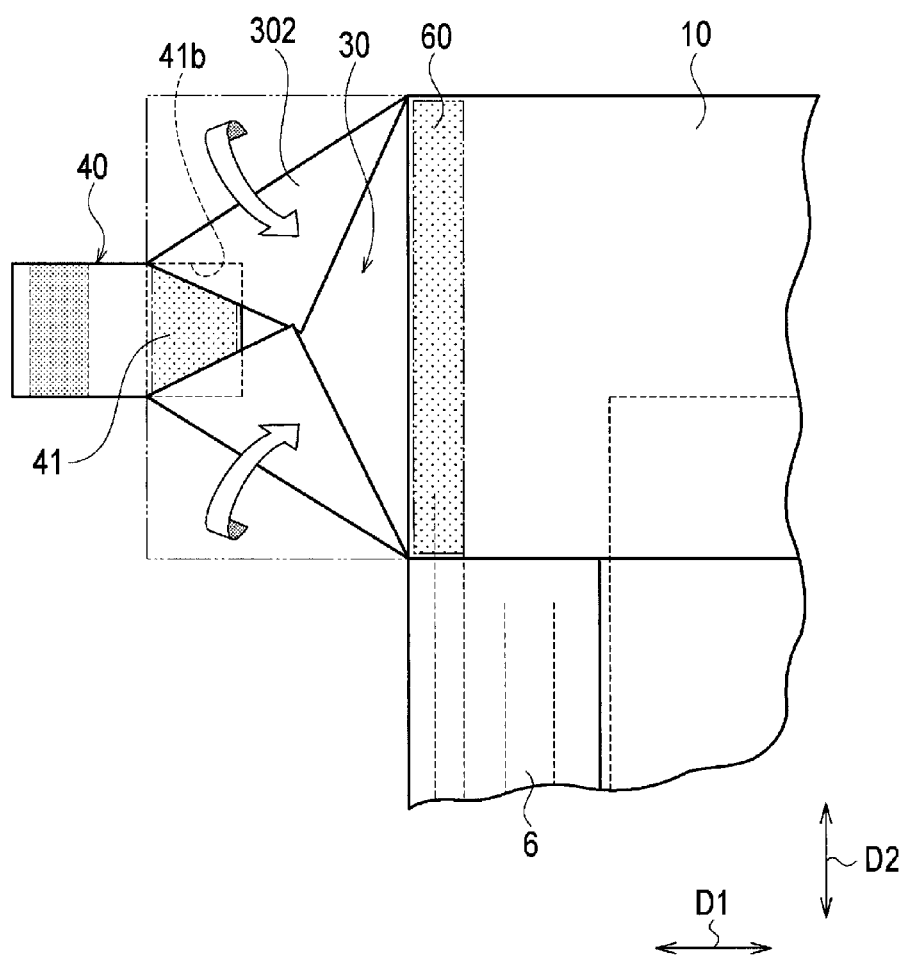
[FIG. 8]

FIG. 8 shows another modification of the back-side side flap 30. As shown in FIG. 8, similar to the leg periphery side region 301, the body side region 302 is foldable onto the tape fastener 40 along a further folding line d2 to cover an upper end portion 41b, adjacent the body $W_B$ (see FIG. 3), of the tape attaching part 41, in response to the stress generated when the tape fasteners 40 is engaged, while being pulled, with the end portion 10a2 of the inner part 10.

According to the third modification, discomfort or unpleasant feeling to the wearer W due to direct contact of the tape fastener 40 with the body $W_B$ of the wearer W can be further avoided.

Fourth Modification

Figure 9:
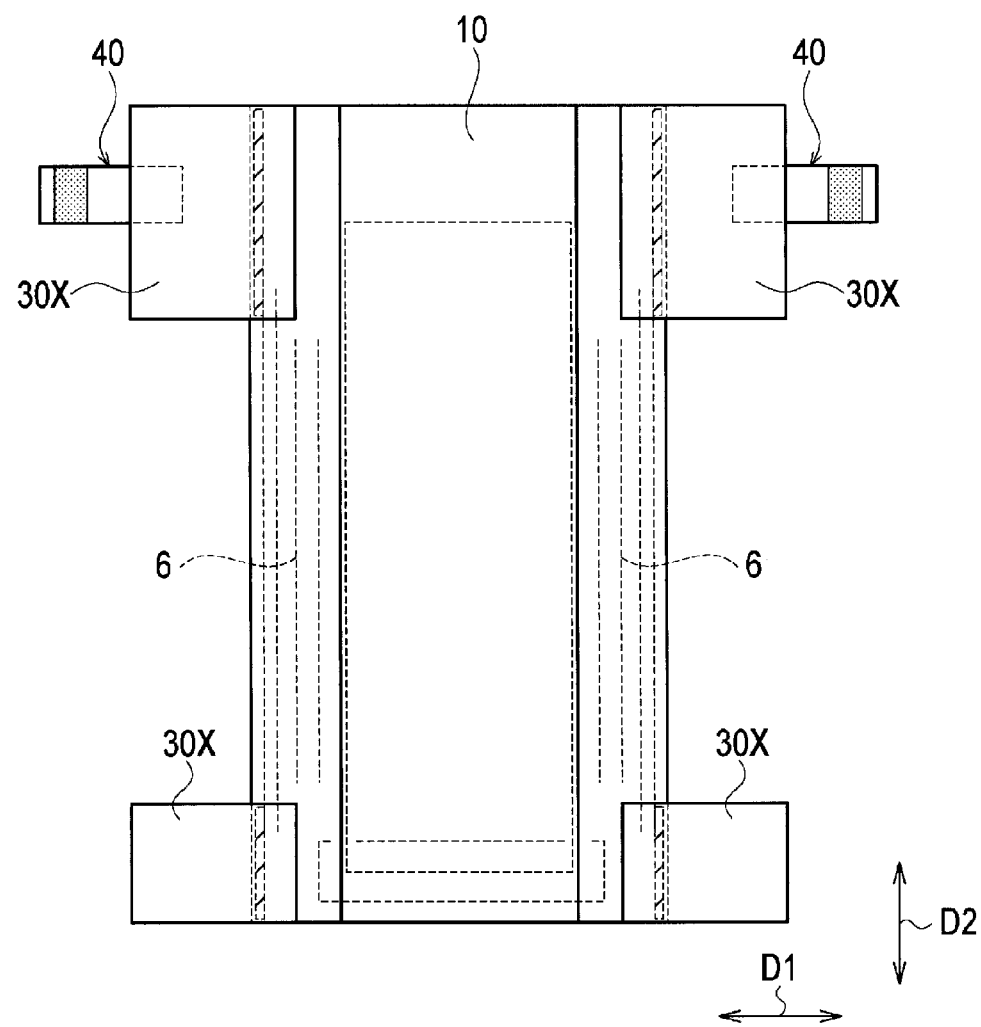
[FIG. 9]

FIG. 9 shows a modification in the shape of the side flap(s). As shown in FIG. 9, a side flap bonded to the inner part 10 need not be an integral side flap that extends across an entire width of the inner part 10 as described above. Instead, separate right and left side flaps each projecting outwardly from only one of the end portions 10b1, 10b2 of the inner part 10 in the width direction D1 are provided. A disposable diaper according to this modification includes a pair of right and left back-side side flaps 30X, and/or a similar pair of right and left abdominal-side side flaps 31X.

Any one of the back-side and the abdominal-side side flaps may be formed as separate right and left side flaps, depending on the manufacturing cost, the strength required in the disposable diaper, or other considerations.

Fifth Modification

Figure 10:
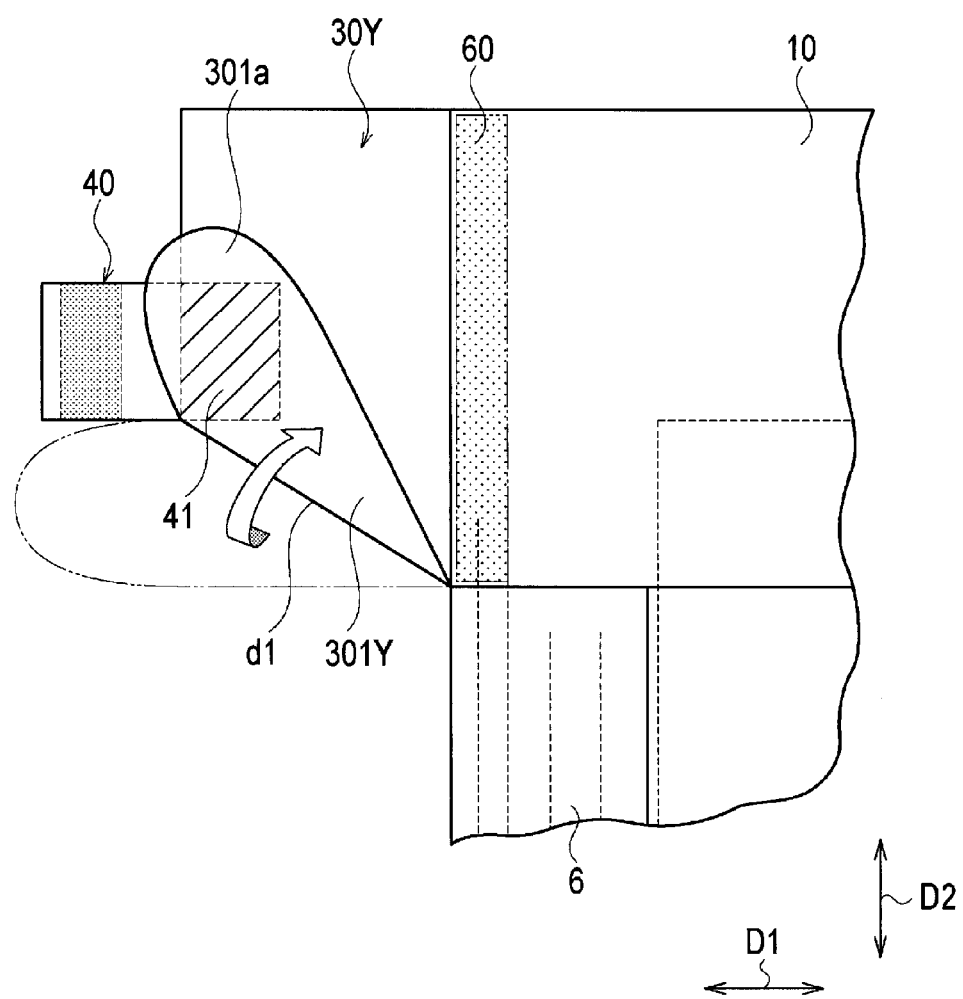
[FIG. 10]
Figure 11:
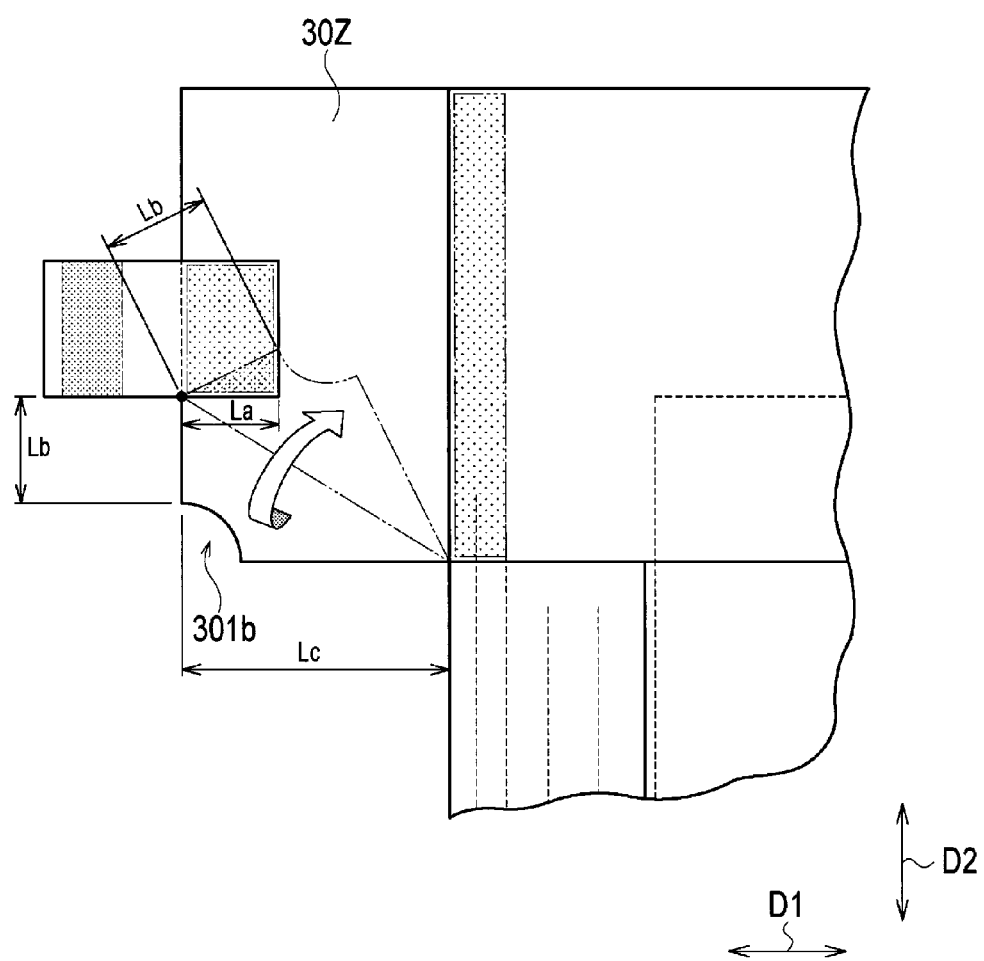
[FIG. 11]

FIGS. 10 and 11 show other modifications in the side flap shape. As shown in FIG. 10, a side flap need not be rectangular in shape like the back-side side flap 30 mentioned above, and may be of a shape having a projecting portion 301a (corresponding to the leg periphery side region 301) that projects outward in the width direction D1 as in a back-side side flap 30Y.

According to such a modification, when the back-side side flap 30 is folded along the folding line d1, the projecting portion 301a covers the entire tape attaching part 41 of the tape fasteners 40, so that discomfort or unpleasant feeling to the wearer W can be further surely avoided.

Likewise, as shown in FIG. 11, a side flap need not be rectangular in shape like the back-side side flap 30, and may be of a shape like a back-side side flap 30Z with a cutout 301b formed by cutting a part of the leg periphery side region 301 of the back-side side flap 30. The back-side side flap 30Z still satisfies the relationship of La<Lb<Lc.

Although the disposable diaper for an infant or toddler has been described as an example, the present invention is applicable also to a disposable diaper for an adult. In addition, although the tape fastener 40 is attached to the back-side side flap 30, the tape fastener 40 may be attached to the abdominal-side side flap 31.

Note that the entire contents of the Japanese Patent Application No. 2009-229091, filed on Sep. 30, 2009 is incorporated herein by reference.

Further, the aspects of the present invention may be arranged described in at least the following items. In the disposable diaper, said side flap may comprise alternatingly arranged regions of different rigidities to define a folding line along which the leg periphery side region is foldable upwardly in response to said stress.

The disposable diaper may comprise an inner part having a longitudinal direction and a width direction orthogonal to the longitudinal direction, said inner part including a liquid permeable top sheet, a liquid impermeable back sheet, and an absorber provided between the top sheet and the back sheet; a side flap at one of end portions of the inner part in the longitudinal direction and connected to at least one of end portions of the inner part in the width direction; and a tape fastener attached to a side end portion of the side flap and for engaging with the other end portion of the inner part in the longitudinal direction; wherein the tape fastener includes a tape attaching part attached to the side flap and exposed at an outer side face of the side flap, the side flap includes a leg periphery side region adapted to be positioned closer to a leg of a wearer than the tape attaching part when the disposable diaper is fitted onto the wearer, and said side flap has a flexural rigidity lower than that of the tape fastener and in a KB value range from about 0.1 to about 1 gf, such that the leg periphery side region is foldable upwardly along a folding line, that extends obliquely upwardly from a boundary between the inner part and the side flap to a lower end portion of the tape attaching part, to cover at least partially said lower end portion of the tape attaching part to prevent said lower end portion of the tape attaching part from directly contacting the wearer's skin.

In the disposable diaper, said side flap may comprise alternatingly arranged regions of different rigidities to define said folding line. In the disposable diaper, a basic weight of the tape fastener may not less than 1.5 times and not more than 5 times a basic weight of the side end portion where the tape fastener is attached to the side flap.

In the disposable diaper, said side flap may be defined by a liquid-impermeable sheet which is other than the back sheet, extends across an entire width of the inner part, and is directly attached to an inner side face of said end portion of the inner part in the longitudinal direction to be in direct contact with the wearer, in use.

In the disposable diaper, the side flap may partially cover said one of the end portions of the inner part in the longitudinal direction, and projects outwardly beyond only one of the end portions of the inner part in the width direction; the diaper may further comprising a further side flap which partially covers said one of the end portions of the inner part in the longitudinal direction, and projects outwardly beyond the other one of the end portions of the inner part in the width direction.

In the disposable diaper, the side flap may include a body side region adapted to be positioned closer to a waistline of the wearer than the tape attaching part, and the body side region may be foldable downwardly along a further folding line, that extends obliquely downwardly from the boundary between the inner part and the side flap to an upper end portion of the tape attaching part, to cover at least partially said upper end portion of the tape attaching part, thereby preventing the upper end portion of the tape attaching part from directly contacting the wearer's skin.

In the disposable diaper, the leg periphery side region of said side flap, when folded along said folding line, may entirely cover the tape attaching part of the tape fastener.

In the disposable diaper, the leg periphery side region of said side flap may be configured to project into a leg hole of the diaper to be folded upwardly along said folding line upon direct contact with the wearer's leg in use.

The disposable diaper may comprise an inner part having a longitudinal direction and a width direction orthogonal to the longitudinal direction, said inner part including a liquid permeable top sheet, a liquid impermeable back sheet, and an absorber provided between the top sheet and the back sheet; a side flap at one of end portions of the inner part in the longitudinal direction and connected to both end portions of the inner part in the width direction; and a pair of tape fasteners each of which includes a tape attaching part attached to an outer side face of the side flap and is engageable with the other end portion of the inner part in the longitudinal direction to define a waist hole and a pair of leg holes; wherein the side flap includes leg periphery side regions each being arranged to project into the respective leg hole, to be folded upwardly upon direct contact with a wearer's leg in use, and to cover at least partially the respective tape attaching part to prevent the tape attaching part from directly contacting the wearer's skin.

Further, the aspects of the present invention described above may be arranged in at least the following item.

A disposable diaper comprising: an inner part comprising a liquid permeable topsheet, a liquid impermeable backsheet and an absorber provided between the topsheet and the backsheet, the inner part extending in a longitudinal direction between a front waist region and a rear waist region and having an inner surface and an outer surface; wherein either the front waist region or the rear waist region is provided with at least one transversely extending side flap that is provided with at least one tape fastener arranged for attachment to an outer surface of the other of the front or the rear waist region; and wherein the side flap is connected to the inner part in the longitudinal direction, and the tape fastener is attached to an outer surface of the side flap, the arrangement being such that, when the tape fastener is attached to the outer surface of the other of the front or the rear waist region, a stress is generated in the side flap, such that a leg periphery side region of the side flap, which extends below the fastener, is folded outwardly to cover at least a portion of the tape fastener.

Additionally, one or more of the following embodiments are provided in accordance with the following, preferred, further aspects, which may be taken alone or in combination with one another:

A bottom edge of the tape fastener may intersect an outer side edge of the side flap at a first point, and an outer side edge of the longitudinal connection, between the side flap and the inner part, may intersect with a bottom edge of the side flap at a second point, to create a folding line between these points about which the side flap is folded.

A high rigidity part, which has a rigidity higher than that of the side flap material, may be provided in the side flap, and comprise one or more lines that extend substantially parallel to the folding line.

The high rigidity part may comprise a line that is formed along the bending line and extends for at least a portion of the distance between the first and second points. The line may extend between the first and second points, so as to join them. The line may be continuous or discontinuous.

The high rigidity part may be formed by heat sealing or embossing.

The longitudinal connection may extend continuously for the length of the side flap in the longitudinal direction. The longitudinal connection may be a bonded part and may comprise hot melt adhesive.

A length Lb of the leg periphery side region in the longitudinal direction may be longer than a length La of the tape attaching part in the width direction.

A length Lc from a boundary of the inner part and the side flap to the corresponding side edge of the side flap may be longer than the length Lb.

A second flexural rigidity may be smaller than a first flexural rigidity, where the first flexural rigidity is a flexural rigidity of a first material which constitutes the tape fastener, and the second flexural rigidity is a flexural rigidity of a second material which constitutes the side flap.

A mass per unit area of a first material, which constitutes the tape fastener, may be not less than 1.5 times and not more than 5 times as much as a mass per unit area of a second material, which constitutes the side flap.

A mass per unit area of a first material, which constitutes the tape fastener, may be within the range from 40 $g/m^2$ to 120 $g/m^2$ and a mass per unit area of a second material, which constitutes the side flap may be in the range of 20 $g/m^2$ to 60 $g/m^2$.

A longitudinal gather may be provided, containing an elongated stretchable member that is provided in a state extended in the longitudinal direction, wherein the gather is provided in a side edge portion of the inner part in the width direction thereof, the side flap has a bonded part bonded to the inner part, and the bonded part is formed closer to the center of the inner part in the width direction thereof than an inner edge of the gather in the width direction.

The side flap may include a body side region, which extends above the fastener and is positioned closer to a waist opening of the diaper than the tape attaching part, the arrangement being such that, when the tape fastener is attached to the outer surface of the other of the front or the rear waist region, a stress is generated in the side flap, such that the body side region of the side flap is folded outwardly to cover at least a portion of the tape fastener.

A top edge of the tape fastener may intersect an outer side edge of the side flap at a third point, and an outer side edge of the longitudinal connection, between the side flap and the inner part, and may intersect with a top edge of the side flap at a fourth point, to create a folding line between these points about which the side flap is folded.

The invention claimed is:

1. A disposable diaper, comprising:
   an inner part having a longitudinal direction and a width direction orthogonal to the longitudinal direction, said inner part including
      a liquid permeable top sheet,
      a liquid impermeable back sheet, and
      an absorber provided between the top sheet and the back sheet;
   a side flap at one of end portions of the inner part in the longitudinal direction and connected to at least one of end portions of the inner part in the width direction;
   a tape fastener attached to a side end portion of the side flap and for engaging with the other end portion of the inner part in the longitudinal direction; and
   a gather including a plurality of elongated stretchable members fixed to the gather in a state where the stretchable members are stretched in the longitudinal direction, wherein
   the tape fastener includes a tape attaching part attached to the side flap and exposed at an outer side face of the side flap,
   the side flap includes a leg periphery side region adapted to be positioned closer to a leg of a wearer than the tape attaching part when the disposable diaper is fitted onto the wearer,
   the leg periphery side region is configured to be folded upwardly to cover at least partially an end portion of the tape attaching part adjacent the leg of the wearer in response to a stress generated when the tape fastener is engaged, while being pulled, with the other end portion of the inner part in the longitudinal direction, whereby said leg periphery side region folded upwardly prevents the end portion of the tape attaching part from directly contacting the wearer's skin,
   the gather is provided in said at least one end portion of the inner part in the width direction,
   the side flap has a bonded part bonded to the inner part, and
   the bonded part is, in the width direction, inboard of an innermost stretchable member among the stretchable members of said gather.

2. The disposable diaper according to claim 1, wherein a length Lb of the leg periphery side region in the longitudinal direction is longer than a length La of the tape attaching part in the width direction.

3. The disposable diaper according to claim 2, wherein a length Lc in the width direction from (i) a boundary between the inner part and the side flap to (ii) the side end portion of the side flap is longer than the length Lb.

4. The disposable diaper according to claim 1, wherein a second flexural rigidity is smaller than a first flexural rigidity, where
   the first flexural rigidity is a flexural rigidity of a first material which constitutes the tape fastener when a predetermined curvature is given to the first material, and
   the second flexural rigidity is a flexural rigidity of a second material which constitutes the side flap when the predetermined curvature is given to the second material.

5. The disposable diaper according to claim 4, wherein a mass per unit area of the first material which constitutes the tape fastener is not less than 1.5 times and not more than 5 times a mass per unit area of the second material which constitutes the side end portion where the tape fastener is attached to the side flap.

6. The disposable diaper according to claim 1, wherein
   the side flap has a high rigidity part having a rigidity higher than other parts of the side flap, and
   the high rigidity part defines a folding line along which the leg periphery side region is foldable upwardly in response to said stress.

7. The disposable diaper according to claim 6, wherein the high rigidity part at least extends obliquely from the end portion of the tape attaching part adjacent the leg periphery portion toward a boundary between the inner part and the side flap.

8. The disposable diaper according to claim 1, wherein
   the side flap includes a body side region adapted to be positioned closer to a waistline of the wearer than the tape attaching part, and
   the body side region is foldable downwardly to cover at least partially the end portion of the tape attaching part adjacent the waistline of the wearer in response to the stress, thereby further preventing the end portion of the tape attaching part from directly contacting the wearer's skin.

9. The disposable diaper according to claim 1, wherein
   the tape fastener extends in the width direction, and
   the leg periphery side region is configured to be folded in response to the stress generated when the tape fastener is pulled in the width direction.

10. A disposable diaper, comprising:
    an inner part having a longitudinal direction and a width direction orthogonal to the longitudinal direction, said inner part including
       a liquid permeable top sheet,
       a liquid impermeable back sheet, and
       an absorber provided between the top sheet and the back sheet;
    a side flap at one of end portions of the inner part in the longitudinal direction and connected to at least one of end portions of the inner part in the width direction; and
    a tape fastener attached to a side end portion of the side flap and for engaging with the other end portion of the inner part in the longitudinal direction;
    wherein
    the tape fastener includes a tape attaching part attached to the side flap and exposed at an outer side face of the side flap,
    the side flap includes a leg periphery side region adapted to be positioned closer to a leg of a wearer than the tape attaching part when the disposable diaper is fitted onto the wearer,
    the leg periphery side region is configured to be folded upwardly to cover at least partially an end portion of the tape attaching part adjacent the leg of the wearer in response to a stress generated when the tape fastener is engaged, while being pulled, with the other end portion of the inner part in the longitudinal direction, whereby said leg periphery side region folded upwardly prevents the end portion of the tape attaching part from directly contacting the wearer's skin, and said side flap has a flexural rigidity lower than that of the tape fastener, such that the leg periphery side region is foldable upwardly along a folding line, that extends obliquely upwardly from a boundary between the inner part and the side flap to a lower end portion of the tape attaching part, to cover at least partially said lower end portion of the tape attaching part to prevent said lower end portion of the tape attaching part from directly contacting the wearer's skin.

11. The disposable diaper according to claim 10, wherein said side flap comprises alternatingly arranged regions of different rigidities to define said folding line.

12. The disposable diaper according to claim 10, wherein a basic weight of the tape fastener is not less than 1.5 times and not more than 5 times a basic weight of the side end portion where the tape fastener is attached to the side flap.

13. The disposable diaper according to claim 10, wherein said side flap is defined by a liquid impermeable sheet which is other than the back sheet, extends across an entire width of the inner part, and is directly attached to an inner side face of said end portion of the inner part in the longitudinal direction to be in direct contact with the wearer, in use.

14. The disposable diaper according to claim 10, wherein the side flap partially covers said one of the end portions of the inner part in the longitudinal direction, and projects outwardly beyond only one of the end portions of the inner part in the width direction;

the diaper further comprising a further side flap which partially covers said one of the end portions of the inner part in the longitudinal direction, and projects outwardly beyond the other one of the end portions of the inner part in the width direction.

15. The disposable diaper according to claim 10, wherein the side flap includes a body side region adapted to be positioned closer to a waistline of the wearer than the tape attaching part, and the body side region is foldable downwardly along a further folding line, that extends obliquely downwardly from the boundary between the inner part and the side flap to an upper end portion of the tape attaching part, to cover at least partially said upper end portion of the tape attaching part, thereby preventing the upper end portion of the tape attaching part from directly contacting the wearer's skin.

16. The disposable diaper according to claim 10, wherein the leg periphery side region of said side flap, when folded along said folding line, entirely covers the tape attaching part of the tape fastener.

17. The disposable diaper according to claim 15, wherein said side flap has a flexural rigidity in a KB value range from about 0.1 to about 1 gf.

* * * * *